(12) United States Patent
Ibert et al.

(10) Patent No.: US 10,501,560 B2
(45) Date of Patent: Dec. 10, 2019

(54) LOW-VISCOSITY STARCH HYDROLYSATE WITH IMPROVED RETROGRADATION BEHAVIOUR

(71) Applicant: ROQUETTE FRERES, Lestrem (FR)

(72) Inventors: Mathias Ibert, La Chapelle D'armentieres (FR); Aline Lecocq, La Madeleine (FR); Pierre Lanos, La Bassee (FR)

(73) Assignee: Roquette Freres, Lestrem (FR)

(*) Notice: Subject to any disclaimer, the term of this patent is extended or adjusted under 35 U.S.C. 154(b) by 0 days.

(21) Appl. No.: 15/781,251

(22) PCT Filed: Dec. 12, 2016

(86) PCT No.: PCT/FR2016/053326
§ 371 (c)(1),
(2) Date: Jun. 4, 2018

(87) PCT Pub. No.: WO2017/098191
PCT Pub. Date: Jun. 15, 2017

(65) Prior Publication Data
US 2018/0319900 A1    Nov. 8, 2018

(30) Foreign Application Priority Data
Dec. 10, 2015  (FR) .................................. 15 62123

(51) Int. Cl.
| | | |
|---|---|---|
| C08B 30/18 | (2006.01) | |
| C08L 3/02 | (2006.01) | |
| A23L 29/212 | (2016.01) | |
| A23L 29/30 | (2016.01) | |
| C12P 19/14 | (2006.01) | |

(Continued)

(52) U.S. Cl.
CPC ............ *C08B 30/18* (2013.01); *A23L 29/212* (2016.08); *A23L 29/35* (2016.08); *C08L 3/02* (2013.01); *C12P 19/14* (2013.01); *A61K 47/26* (2013.01); *A61K 47/36* (2013.01)

(58) Field of Classification Search
None
See application file for complete search history.

(56) References Cited

U.S. PATENT DOCUMENTS 3,582,359 A * 6/1971 Horn et al. ................... 426/573
6,068,705 A * 5/2000 Tang ....................... C08B 30/12
                                                            106/215.5

(Continued)

FOREIGN PATENT DOCUMENTS

FR    2 203 877 A1    5/1974
FR    2 762 616 A1    10/1998

(Continued)

OTHER PUBLICATIONS

The International Search Report, dated May 3, 2017, in the corresponding PCT Appl. No. PCT/FR2016/053326.

*Primary Examiner* — Melvin C. Mayes
*Assistant Examiner* — Stefanie J Cohen

(57) ABSTRACT

The invention relates to a starch hydrolysate having a Dextrose Equivalent DE of between 5 and 30 and a specific carbohydrate profile. In particular, the hydrolysate of the invention has improved retrogradation behaviour. The invention also relates to a method for the production of said starch hydrolysate.

23 Claims, 8 Drawing Sheets
Specification includes a Sequence Listing.

(51) Int. Cl.
*A61K 47/26* (2006.01)
*A61K 47/36* (2006.01)

(56) References Cited

U.S. PATENT DOCUMENTS

| | | |
|---|---|---|
| 6,284,498 B1 | 9/2001 | Fouache et al. |
| 7,273,740 B2 | 9/2007 | Callen et al. |
| 7,612,198 B2 * | 11/2009 | Fuertes .................. C08B 30/12 536/102 |
| 7,659,102 B2 | 2/2010 | Callen et al. |
| 7,666,633 B2 | 2/2010 | Callen et al. |

FOREIGN PATENT DOCUMENTS

| | | | |
|---|---|---|---|
| GB | 2 001 075 A | 1/1979 | |
| GB | 2001075 A * | 1/1979 | ............. C12P 19/14 |
| WO | 01/96537 A2 | 12/2001 | |
| WO | 2004/064540 A1 | 8/2004 | |
| WO | 2009/137839 A1 | 5/2008 | |
| WO | 2011/017093 A1 | 2/2011 | |
| WO | 2013/116175 A2 | 8/2013 | |

* cited by examiner

LOW-VISCOSITY STARCH HYDROLYSATE WITH IMPROVED RETROGRADATION BEHAVIOUR

CROSS-REFERENCE TO RELATED APPLICATIONS

This application is a National Stage Application of PCT/FR2016/053326 filed Dec. 12, 2016, which claims priority from French Patent Application No. 15 62123, filed on Dec. 10, 2015. The priority of said PCT and French Patent Application are claimed. Each of the prior mentioned applications is hereby incorporated by reference herein in its entirety.

FIELD OF THE INVENTION

A subject of the invention is a novel starch hydrolysate having a dextrose equivalent (DE) of less than 30 with improved properties. Another subject of the invention relates to a process for producing this hydrolysate. A subject of the invention is also the use of this hydrolysate in the food and pharmaceutical industries.

The objective of the invention is more specifically to provide a starch hydrolysate with good retrogradation behavior, while at the same time retaining a more neutral and not very sweet taste and odor, and also an improved texture in the mouth.

PRIOR ART

Starch hydrolysates are generally grouped together in two major families: maltodextrins when they have a low DE, generally less than 20, and glucose syrups when they have a DE of 20 or more.

These hydrolysates are produced in the form of syrups from starch in aqueous suspension, said starch being burst by heating and hydrolyzed in the presence of acid, of enzyme or a mixture of acid and enzyme, so as to convert the starch into carbohydrates of lower molecular weight. At the end of this process, a syrup is obtained which can optionally be spray-dried.

The composition of the hydrolysate (or else carbohydrate profile) depends on the starting starch used, but also on the hydrolysis process used. For example, the conversion of the starch is carried out by means of a first hydrolysis step, commonly known as "liquefaction".

The hydrolysis can be stopped after this step in order to obtain maltodextrins, the DE of which is easily adjusted by those skilled in the art by varying the operating conditions (time, temperature, choice and amounts of enzymes and/or of pH, etc.). Compared with glucose syrups, these maltodextrins are weakly sweet.

Conversely, it is possible to leave the hydrolysis to continue in order to obtain glucose syrups, which generally have a sweeter taste. These glucose syrups are generally produced by means of a second hydrolysis step, commonly known as "saccharification". This step is generally carried out at lower temperature than the liquefaction step and under different operating conditions, for example by adding one or more enzymes.

In the event of the use of enzymes in the process, their selection is obviously essential with regard to the carbohydrate profile of the hydrolysate obtained.

Among the enzymes that can be used in processes for producing glucose syrups are the alpha-amylase enzymes sold relatively recently by the company Verenium under the brand names Veretase® and Fuelzyme®-LF. The enzymatic function of these alpha-amylase enzymes is to hydrolyze particularly the high-molecular-weight saccharides; this makes it possible in particular to very rapidly reduce the viscosity of the starch hydrolysate.

In the remainder of the description, for reasons of simplicity, these alpha-amylase enzymes which hydrolyze particularly the high-molecular-weight saccharides are grouped together under the term "Enzyme V".

The Enzymes V sold by the company Verenium under the brand names Veretase® and Fuelzyme®-LF are enzymes chosen from the polypeptides encoded by a nucleotide sequence as represented in SEQ ID NO1 or a nucleotide sequence having a percentage identity relative to the sequence SEQ ID NO1 which is at least equal to 80%, preferentially 85%, preferentially 90%, more preferentially 98%, even more preferentially 99%.

The sequence SEQ ID NO1 represents a nucleotide sequence encoding an alpha-amylase. This sequence is available online under GenBank accession number AF504065.1.

These enzymes V are also described in patents U.S. Pat. Nos. 7,273,740, 7,666,633 and 7,659,102. These documents also describe processes for producing syrups very rich in glucose (the glucose content of which is greater than 95%), these processes comprising a liquefaction step using an Enzyme V and also a saccharification step using this enzyme together with an additional enzyme of glucoamylase type.

Likewise, among the documents describing the production of hydrolysates using an Enzyme V, mention may be made of application WO 2009/137839, which describes essentially hydrolysates which are glucose syrups. These hydrolysates having a DE ranging from 20 to 52, of low viscosity, comprise a sugar content of less than 25%. These syrups are of low viscosity since they comprise a low amount of polysaccharides having a DP greater than or equal to 15, together with a high amount of oligosaccharides having a DP ranging from 3 to 14. Among the numerous variants of production of these hydrolysates is the embodiment of example 18; the latter describes a glucose syrup produced by a process comprising a step of liquefaction of starch in the presence of an amylase of Enzyme V type, followed by a saccharification step using this enzyme together with additional enzymes which are an isoamylase and a pullulanase. The syrups obtained have a DE of 29 or 30 and comprise a zero amount of polysaccharides having a DP greater than or equal to 15.

Document WO 2013/116175 describes, for its part, in the same way, a process for producing a glucose syrup comprising a step of hydrolysis of the starch using an Enzyme V in order to obtain, before the filtration step, a hydrolysate which has a carbohydrate profile such that the amounts of DP1-2 range from 10% to 25%, the amounts of DP3-11 range from 70% to 90% and the amounts of DP12 and higher are less than 15%. These syrups also have the same advantages: a reduced content of sugars compared with a glucose syrup having a higher DE, while at the same time having a similar viscosity.

The mixture of alpha-amylases described in application WO 2011/017093 relates to a mixture of an Enzyme V and of a *Bacillus licheniformis* enzyme, these enzymes being in relative amounts ranging from 0.5 to 5 Liquefon Units (LUs) of *Bacillus licheniformis* per 5 Modified Wohlgemuth Units (MWUs) Enzyme V. This mixture aims to solve the following problem: when a syrup very rich in glucose is produced by carrying out a liquefaction step using exclusively an Enzyme V as alpha-amylase, the syrup very rich in glucose obtained at the end of the saccharification shows positive results in the iodine test, thereby indicating that the starch hydrolysis is incomplete. This document describes the production of glucose syrups having a high DE, produced by a process comprising a step of liquefaction of starch in the presence of the mixture of alpha-amylase of Enzyme V and *Bacillus licheniformis* type followed by a saccharification step using this enzyme mixture together with an additional glucoamylase and pullulanase enzyme mixture (Optimax® 4060 VHP).

The starch hydrolysates are in most cases dissolved before being used, for example in the production of foods. With regard to the starch hydrolysates obtained by means of conventional alpha-amylases, for example the Liquozyme® Supra (Novozymes®) enzyme, one of the recurring problems is that they may not be stable when dissolved. This is known as a retrogradation phenomenon. The hydrolysate solution then becomes non-homogeneous, which makes its subsequent use complex and generally requires redissolving of the retrograded hydrolysate before being able to use the hydrolysate solution. This phenomenon is generally observed after a few days. However, this hydrolysate retrogradation phenomenon is seen more rapidly for hydrolysates having a DE of less than 10, particularly when the DE is less than 5.

It is noted from the aforementioned that, while processes for producing glucose syrups using an Enzyme V during the liquefaction step have already been described, it is noted that none of these documents showed interest in the problem of starch hydrolysate retrogradation.

In point of fact, contrary to the hydrolysates obtained using conventional alpha-amylases, the applicant has noted that, surprisingly, hydrolysates having a DE of 30 or less and which are produced by a process comprising a starch liquefaction step using an Enzyme V, rapidly retrograde. This retrogradation phenomenon can be observed in the case of hydrolysates having a DE of less than or equal to 30 and it is most particularly observed in the case of maltodextrins having a DE of less than 20.

In the context of its research, the applicant has succeeded in producing a novel starch hydrolysate having good retrogradation behavior, while at the same time retaining a viscosity that is lower than hydrolysates having an equivalent DE which are produced using conventional alpha-amylases (other than an Enzyme V). This hydrolysate is characterized by an entirely specific carbohydrate profile.

SUMMARY OF THE INVENTION

The invention thus relates to a starch hydrolysate having a Dextrose Equivalent DE ranging from 5 to 30 and in which the DE, the dry weight content of saccharides having a degree of polymerization ranging from 10 to 20 (DP 10-20) and the dry weight content of saccharides having a degree of polymerization of 50 or more (DP 50+) are such that they meet the following inequations:

$$-0.83 \times DE + 25 \leq \% \ DP50+ \leq -1.07 \times DE + 40;$$

$$-0.83 \times DE + 27.5 \leq \% \ DP\ 10\text{-}20 \leq -1.25 \times DE + 55.$$

The hydrolysate according to the invention has, surprisingly, very good retrogradation behavior.

It also has the advantage, when it is dissolved, of having a low viscosity. This allows it to be easily handled and used as raw material in food and pharmaceutical products. It also has other advantages, such as a neutral taste and odor, the fact that it is not very sweet owing to the DE thereof but sweeter than conventional hydrolysates, and a very good texture in the mouth.

The applicant has succeeded in producing the hydrolysate according to the invention by carrying out a specific process.

The invention thus relates to a process for producing a starch hydrolysate, comprising:
  a) a step of bringing an aqueous solution of starch or of starchy material into contact with at least one alpha-amylase chosen from the Enzymes V;
  b) followed by a step of hydrolysis of said aqueous solution;
  c) followed by a step of inhibition of the Enzyme V so as to form a solution of intermediate hydrolysate having a DE equal to $DE_c$;
  d) followed by a step of bringing the solution of intermediate hydrolysate obtained in step c) into contact with at least one additional alpha-amylase, different than the Enzyme V;
  e) followed by a second hydrolysis step so as to form a hydrolysate for a period of time sufficient for it to have a Dextrose Equivalent $DE_e$ ranging from 5 to 30;
  f) followed by a step of recovering the hydrolysate formed in step e);

characterized in that the Enzyme V is an enzyme chosen from:
  the polypeptides encoded by a nucleotide sequence as represented in SEQ ID NO1 or a nucleotide sequence having a percentage identity relative to the sequence SEQ ID NO1 at least equal to 80%, preferentially 85%, preferentially 90%, more preferentially 98%, even more preferentially 99%, or
  the polypeptides comprising the enzymatically active fragment of the sequence encoded by the sequence SEQ ID NO1.

According to one variant of the invention, the Enzyme V is an enzyme showing a result in the test A of less than 10%, the test A consisting in:
  carrying out a step of hydrolysis at a pH of 5.3 of a native corn starch with, as sole enzyme, the enzyme to be tested, until a starch hydrolysate having a DE equal to 20 is obtained,
  determining the content of DP50+ of said hydrolysate, the result in the test A being equal to this content of DP50+.

Contrary to the enzymes mentioned in documents FR 2 203 877 A1, GB 2 001 075 A, WO 01/96537 A2, EP 0 905 256 A1, WO 2004/064540 A1 and FR 2 762 616 A1, the Enzyme V of the invention thus makes it possible to very greatly reduce the content of DP50+ saccharides in comparison with the conventional enzymes. Among the conventional enzymes, mention may be made of the Termamyl 120 L enzyme.

As shown in the examples, this specific process, using this specific Enzyme V, has made it possible to obtain the specific carbohydrate profile of the hydrolysate of the invention.

The hydrolysate exhibits in particular a sweeter taste, in comparison with a hydrolysate having the same DE and produced using a conventional enzyme of Termamyl type, this being the case even though the sugar contents (that is to say DP1 and DP2 contents) are very similar.

The invention will now be described in detail in the remainder of the description.

DETAILED DESCRIPTION OF THE FIGURES

DETAILED DESCRIPTION OF THE INVENTION

Figure 1:
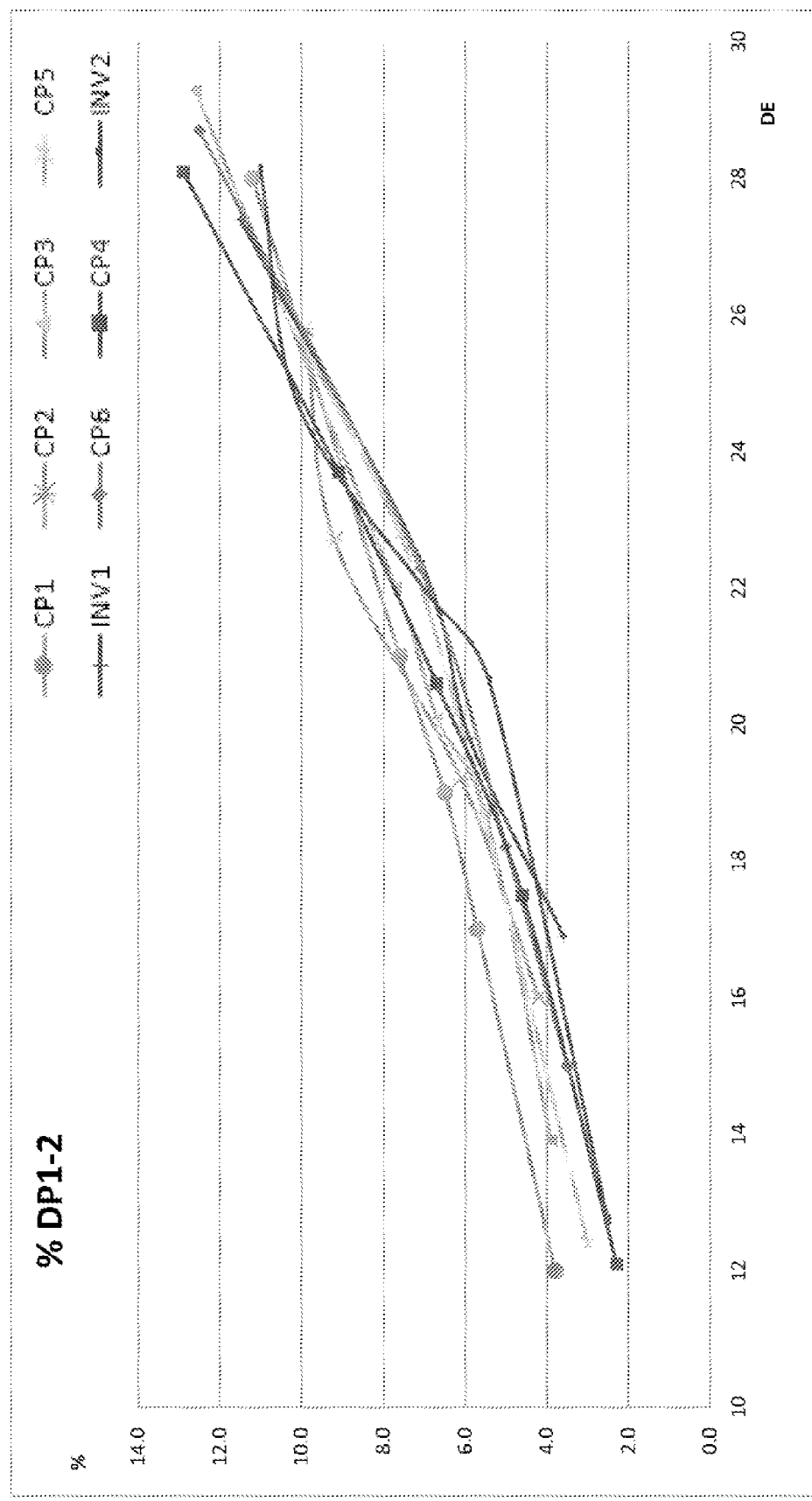
FIG. 1 represents the change in the dry weight content of DP1-2 as a function of the DE of hydrolysates according to the invention and comparative hydrolysates.

The invention relates to a specific starch hydrolysate which will subsequently be described in detail.

The hydrolysate according to the invention has a Dextrose Equivalent (DE) ranging from 5 to 30. The DE defines the degree of hydrolysis of the starch. More particularly, the DE, expressed as percentages, is determined by measuring the reducing capacity of the starch hydrolysate in comparison with the reducing capacity of glucose. The DE can be measured using the NF EN ISO 5377:1981 method.

The carbohydrate profile of the hydrolysate has a specific saccharide distribution.

The term "saccharides" includes, according to the invention, all types of saccharides, that is to say monosaccharides, disaccharides, oligosaccharides and polysaccharides.

According to the invention, the term "DP X" is used to define saccharides and this distribution, in which term X represents the number of glucose units in the saccharide. Likewise, the saccharides having a degree of polymerization comprising a number of glucose units ranging from X to Y (X and Y included) are grouped together under the term "saccharides of DP X-Y".

Furthermore, the saccharides having a degree of polymerization comprising a number of glucose units greater than X (X not included) are grouped together under the term "saccharides of DP X+".

The term "high-molecular-weight saccharides" is intended to mean DP50+ saccharides.

The composition of the invention comprises, according to its DE, specific contents of saccharides of DP 10-20 and of saccharides of DP 50+. The saccharide contents are expressed by dry weight, that is to say that they express the dry weight amount of these saccharides relative to the dry weight amount of all of the saccharides in the hydrolysate.

These contents can be determined by high performance liquid chromatography (HPLC) on ion-exchange resin and by size exclusion chromatography (SEC). The HPLC apparatus can be equipped with a styrene divinylbenzene ion-exchange resin column in silver form, for example a column of Bio-Rad HPX 42A type, and with a refractive index detector. The SEC apparatus can be equipped with polyhydroxymethyl methacrylate polymer columns, for example equipped with OHpak SB-802 HQ, OHpak SB-803 HQ and OHpak SB-805 HQ columns placed in this order.

The SEC apparatus can be calibrated using pullulan standards. Sample preparation and measuring protocols are presented in the Examples section.

For the saccharides of DP X-Y, the content of which ranges up to 19, the content is determined directly by HPLC. With regards to the saccharides of DP X-Y, of which the DP is 20 or more (DP 20-30, DP 31-40, DP 41-50 and DP50+), their contents are determined in the following way:
- the DP 20+ content is determined by HPLC according to the method above;
- the (DP X-Y/DP20+) ratio is determined by SEC according to the method above;
- the DP X-Y content is determined by the following formula:

DP $X$-$Y$=DP 20+×(DP$X$-$Y$/DP20+ ratio).

According to a first variant of the invention, the starch hydrolysate has a Dextrose Equivalent DE ranging from 5 to 30 and in which the DE, the dry weight content of saccharides having a degree of polymerization ranging from 10 to 20 (DP 10-20) and the dry weight content of saccharides having a degree of polymerization of 50 or more (DP 50+) are such that they meet the following inequations:

−0.83×DE+25≤% DP 50+≤−1.07×DE+40;

−0.83×DE+27.5≤% DP 10-20≤−1.25×DE+55.

Preferably, the DE of the hydrolysate of the invention is less than 20, most preferentially ranges from 10 to 19.5.

In these DE ranges, the retrogradation behavior is even more improved compared with a hydrolysate having the same DE, produced by a process comprising a starch liquefaction step using an Enzyme V.

According to a second variant of the invention, the starch hydrolysate has:
- a DE ranging from 24 to 30;
- a dry weight content of DP 10-20 ranging from 10% to 18%;
- a dry weight content of DP 50+ ranging from 3% to 13%.

According to this preferred second variant, the starch hydrolysate advantageously has:
- a dry weight content of DP 1-2 ranging from 6% to 14%;
- and/or a dry weight content of DP 3-6 ranging from 35% to 55%;
- and/or a dry weight content of DP 7-9 ranging from 5% to 25%;
- and/or a dry weight content of DP 21-30 ranging from 2% to 8%;
- and/or a dry weight content of DP 31-40 ranging from 1% to 4%;
- and/or a dry weight content of DP 41-50 ranging from 1% to 4%.

According to a third variant of the invention, the starch hydrolysate has:
- a DE ranging from 20 to 24;
- a dry weight content of DP 10-20 ranging from 10% to 20%;
- a dry weight content of DP 50+ ranging from 6% to 18%.

According to this preferred third variant, the starch hydrolysate advantageously has:
- a dry weight content of DP 1-2 ranging from 4% to 10%;
- and/or a dry weight content of DP 3-6 ranging from 25% to 50%;
- and/or a dry weight content of DP 7-9 ranging from 13% to 30%;

and/or a dry weight content of DP 21-30 ranging from 2% to 8%;
and/or a dry weight content of DP 31-40 ranging from 2% to 5%;
and/or a dry weight content of DP 41-50 ranging from 1% to 4%.

According to a fourth variant, the starch hydrolysate has:
a DE ranging from 17 to 20;
a dry weight content of DP 10-20 ranging from 12% to 25%;
a dry weight content of DP 50+ ranging from 10% to 19%.

According to this preferred fourth variant, the starch hydrolysate advantageously has:
a dry weight content of DP 1-2 ranging from 2% to 7%;
and/or a dry weight content of DP 3-6 ranging from 15% to 35%;
and/or a dry weight content of DP 7-9 ranging from 17% to 26%;
and/or a dry weight content of DP 21-30 ranging from 3% to 10%;
and/or a dry weight content of DP 31-40 ranging from 2% to 6%;
and/or a dry weight content of DP 41-50 ranging from 2% to 4%.

According to a fifth variant, the starch hydrolysate has:
a DE ranging from 15 to 17;
a dry weight content of DP 10-20 ranging from 16% to 27%;
a dry weight content of DP 50+ ranging from 13% to 22%.

According to this preferred fifth variant, the starch hydrolysate advantageously has:
a dry weight content of DP 1-2 ranging from 2% to 6%;
and/or a dry weight content of DP 3-6 ranging from 16% to 25%;
and/or a dry weight content of DP 7-9 ranging from 17% to 24%;
and/or a dry weight content of DP 21-30 ranging from 5% to 10%;
and/or a dry weight content of DP 31-40 ranging from 3% to 6%;
and/or a dry weight content of DP 41-50 ranging from 2% to 4%.

According to a sixth variant of the invention, the starch hydrolysate has:
a DE ranging from 13 to 15;
a dry weight content of DP 10-20 ranging from 17% to 30%;
a dry weight content of DP 50+ ranging from 17% to 25%.

According to this preferred sixth variant, the starch hydrolysate advantageously has:
a dry weight content of DP 1-2 ranging from 1% to 5%;
and/or a dry weight content of DP 3-6 ranging from 13% to 23%;
and/or a dry weight content of DP 7-9 ranging from 15% to 23%;
and/or a dry weight content of DP 21-30 ranging from 6% to 12%;
and/or a dry weight content of DP 31-40 ranging from 3% to 7%;
and/or a dry weight content of DP 41-50 ranging from 2% to 4%.

According to a seventh variant of the invention, the starch hydrolysate has:
a DE ranging from 10 to 13;
a dry weight content of DP 10-20 ranging from 20% to 32%;
a dry weight content of DP 50+ ranging from 18% to 28%.

According to this preferred seventh variant, the starch hydrolysate advantageously has:
a dry weight content of DP 1-2 ranging from 0% to 4%;
and/or a dry weight content of DP 3-6 ranging from 10% to 20%;
and/or a dry weight content of DP 7-9 ranging from 15% to 22%;
and/or a dry weight content of DP 21-30 ranging from 5% to 12%;
and/or a dry weight content of DP 31-40 ranging from 4% to 8%;
and/or a dry weight content of DP 41-50 ranging from 2% to 4%.

According to the invention, the variants 2 to 7 detailed above cannot be combined with one another. Conversely, all of these variants can be combined with the first variant described above.

The advantageous and preferred variants described below can also be combined with the variants 1 to 7.

Generally, the dry weight content of DP11+ is greater than 15%, or even greater than 20%, for example greater than 25%.

Preferably, the dry weight content of DP1-2 ranges from 1% to 15%. Preferably, the dry weight content of DP3-6 ranges from 10% to 60%. Preferably, the dry weight content of DP7-9 ranges from 5% to 30%. Preferably, the dry weight content of DP21-30 ranges from 2% to 15%. Preferably, the dry weight content of DP31-40 ranges from 1% to 6%. Preferably, the dry weight content of DP41-50 ranges from 1% to 4%.

The starch hydrolysate can be a hydrolysate of starch originating from any botanical origin, extracted from the storage organs and tissues of higher plants. This starch can be an amylose-rich starch or, conversely, an amylopectin-rich (waxy) starch. Preferably, the dry content of amylose of the starch ranges from 0% to 85% and the dry content of amylopectin ranges from 15% to 100%. According to the invention, the term "starch" groups together starches and tuber or root starches. The starch may be chosen from starches of cereals such as wheat, corn, barley, triticale, sorghum or rice, tuberous plants such as potato or cassava, or leguminous plants such as pea and soybean, and mixtures of such starches. Preferably, the hydrolysate according to the invention is a hydrolysate of wheat, corn, waxy corn or pea starch, or a hydrolysate of potato starch, most preferentially of wheat, corn or waxy corn starch.

The hydrolysate can in particular be used in the food and pharmaceutical industries, in particular for the production of baby foods, sports drinks, cookies, ice cream, sauces, soups, powdered drinks, icings, carriers for flavorings or sweeteners. The hydrolysate can be used in infant dietetics, in clinical dietetics or in sports dietetics. The hydrolysate can also be used for various fermentations, in particular in the bakery product industry, the brewing industry or the pork meat trade.

The hydrolysate can also be used for the production of a mixture comprising the starch hydrolysate of the invention, in particular a mixture of hydrolysate according to the invention with an additional hydrolysate, this additional hydrolysate possibly being chosen from syrups rich in glucose and/or in maltose.

The hydrolysate of the invention, as emerges in the light of the examples, can be obtained by the specific process of the invention, the various parameters of which are described in detail below; those skilled in the art will know how to easily vary these parameters in order to obtain these hydrolysates according to the invention.

The invention thus relates to a process for producing a starch hydrolysate, comprising:
  a) a step of bringing an aqueous solution of starch into contact with at least one alpha-amylase chosen from the Enzymes V;
  b) followed by a step of hydrolysis of said aqueous solution;
  c) followed by a step of inhibition of the Enzyme V so as to form a solution of intermediate hydrolysate having a DE equal to $DE_c$;
  d) followed by a step of bringing the solution of intermediate hydrolysate obtained in step c) into contact with at least one additional alpha-amylase, different than the Enzyme V;
  e) followed by a second hydrolysis step so as to form a hydrolysate for a period of time sufficient for it to have a Dextrose Equivalent $DE_e$ ranging from 5 to 30;
  f) followed by a step of recovering the hydrolysate formed in step e);
the Enzyme V being an enzyme showing a result in the test A of less than 10%, the test A consisting in:
  carrying out a step of hydrolysis at a pH of 5.3 of a native corn starch with, as sole enzyme, the enzyme to be tested, until a starch hydrolysate having a DE equal to 20 is obtained,
  determining the content of DP50+ of said hydrolysate, the result in the test A being equal to this content of DP50+.

In the first step of the process, a step of bringing an aqueous solution of starch or of starchy material into contact with at least one alpha-amylase chosen from the Enzymes V is carried out.

The starch used for producing the aqueous solution of starch of step a) can be native starch, that is to say starch in granular form obtained by extraction from the storage organs and tissues of the higher plants mentioned above. The starch can also be a starch which has undergone a modification step. This modification step can be a pregelatinization, gelatinization, oxidation or acid hydrolysis step. Preferably, the starch used for producing the aqueous solution of starch is native starch.

The aqueous solution of starch can comprise an amount of starch, expressed by dry weight of starch, ranging from 10% to 50%, preferably ranging from 25% to 40%, for example from 30% to 35%. A granule of native starch comprises bound water. The moisture content of native starch, under standard conditions, varies according to the botanical nature of the starch. Native starch comprises an intrinsic amount of water and the moisture content in this starch is generally between 10% and 20%. By way of example, a native corn starch has a moisture content under standard conditions of approximately 13%, whereas a native potato starch has a moisture content of approximately 18%. The dry weight of the starch can be calculated according to standard ISO 1666:1996.

At least one alpha-amylase chosen from the Enzymes V is introduced into the aqueous solution of starch during step a).

The Enzymes V hydrolyze particularly the high-molecular-weight saccharides. Thus, an Enzyme V is an enzyme which shows in particular a result in the test A of less than 10%, or even less than 5%.

The hydrolysis step of the test A can be carried out at 95° C., optionally after a step of steam-cooking for 5 minutes at 106° C. To carry out the hydrolysis step of the test A, reference may for example be made to the conditions described in protocol 1 of the Examples section of the present application.

The Enzyme V of the invention is an enzyme chosen from:
  the polypeptides encoded by a nucleotide sequence as represented in SEQ ID NO1 or a nucleotide sequence having a percentage identity relative to the sequence SEQ ID NO1 at least equal to 80%, preferentially 85%, preferentially 90%, more preferentially 98%, even more preferentially 99%, or
  the polypeptides comprising the enzymatically active fragment of the sequence encoded by the sequence SEQ ID NO1.

The term "percentage identity" between two nucleic acid sequences or for the purpose of the present invention is intended to denote a percentage of nucleotides between the two sequences to be compared, obtained after the best alignment, this percentage being purely statistical and the differences between the two sequences being distributed randomly and over their entire length. The term "best alignment" or "optimal alignment" is intended to denote the alignment for which the percentage identity determined as below is the highest. The sequence comparisons between two nucleic acid sequences are conventionally carried out by comparing these sequences after having optimally aligned them, said comparison being carried out by segment or by "comparison window" in order to identify and compare the local regions of sequence similarity. The optimal alignment of the sequences for the comparison can be carried out, in addition to manually, by means of the local homology algorithm of Smith and Waterman (1981), by means of the local homology algorithm of Neddleman and Wunsch (1970), by means of the similarity search method of Pearson and Lipman (1988), by means of the computer software using these algorithms (GAP, BESTFIT, BLAST P, BLAST N, FASTA and TFASTA in the Wisconsin Genetics Software Package, Genetics Computer Group, 575 Science Dr., Madison, Wis.). In order to obtain the optimal alignment, the BLAST program is preferably used with the BLOSUM 62 matrix.

The percentage identity between two sequences of nucleic acids is determined by comparing these two optimally aligned sequences, the nucleic acid sequence to be compared possibly comprising additions or deletions with respect to the reference sequence for optimal alignment between these two sequences. The percentage identity is calculated by determining the number of identical positions for which the nucleotide is identical between the two sequences, by dividing this number of identical positions by the total number of positions compared, and by multiplying the result obtained by 100 in order to obtain the percentage identity between these two sequences.

During step a), the Enzyme V is brought into contact with the solution of starch or of starchy material in amounts which make it possible to obtain the DE of the intermediate hydrolysate during step b). This amount can vary a great deal and is directly linked to the conditions used during this step b), in particular the time, the temperature, and/or the pH of the aqueous suspension of starch. The Enzyme V is generally introduced in the form of commercial enzyme solutions. For example, it can be introduced in the form of a solution of Veretase® enzyme sold by the company Verenium®; the solution of Veretase enzyme can be introduced in weight amounts, expressed relative to the dry weight of starch, ranging from 0.01% to 0.5%, preferably from 0.03% to 0.13%. Another way to express the amount of Enzyme V is to express it in amount of enzymatic activity of "Modified Wolgemuth Unit" (MWU) type, well known to those skilled in the art. An MWU unit is the amount of enzyme which makes it possible to hydrolyze one milligram of starch dissolved in a dextrin specific to the MWU test, over the course of thirty minutes and under the standard conditions for using the enzyme. Per gram of dry starch, this amount can be in the range of from 10 to 1000 MWU, for example from 50 to 500 MWU. By way of example, 1 g of a solution of Veretase® enzyme comprises at least 120 000 MWU.

According to one variant of the process, an additional alpha-amylase, different than the Enzyme V, is also brought into contact with the aqueous suspension of starch during step a). This additional alpha-amylase that is different than the Enzyme V can be chosen from the *Bacillus licheniformis* enzymes, in particular those described in application WO 2011/017093 A1. Preferably, the *Bacillus licheniformis* enzymes are chosen from the enzymes of Spezyme® Alpha (Genencor®), LpHera® (Novozymes®), Liquozyme® Supra (Novozymes®) and Termamyl® 120L (Novozymes®) type.

During steps a) and d), the pH of the starch solutions can be increased by adding at least one base or decreased by adding at least one acid, in sufficient amounts so as to select the desired pH. The acid may be organic or inorganic and in particular may be hydrochloric acid. The base may be organic or inorganic and in particular may be sodium hydroxide.

Advantageously, the aqueous solution of starch formed in step a) has a pH ranging from 4.0 to 6.5, advantageously from 4.3 to 5.9.

The aqueous suspension of starch can comprise other additive compounds which assist with the enzymatic hydrolysis. For example, it can also comprise at least one calcium salt, in particular when an additional alpha-amylase which is calcium-dependent is used. The aqueous suspension of starch can also comprise sodium bisulfite.

The aqueous solution of starch can be prepared by simply mixing the constituents.

After the contacting step, the process comprises a hydrolysis step b) so as to form a solution of starch hydrolysate, called "intermediate hydrolysate".

As previously indicated, the duration and the temperature of the hydrolysis step b) depend directly on the pH and on the amount of Enzyme V used during step a), and also on the DE of the intermediate hydrolysate $DE_c$ targeted.

This hydrolysis step b) can be carried out by heating the starch solution prepared in step a). Preferably, the starch solution is heated at a temperature ranging from 75 to 120° C. This step b) is carried out until the starch is sufficiently hydrolyzed, before carrying out the inhibition step c), so as to subsequently be able to obtain the intermediate hydrolysate that is of use in the invention. The duration of this step b) can range from 2 to 300 minutes. This step can be carried out in any type of reactor conventionally used for the hydrolysis of starch, and preferably a stirred reactor.

According to a first variant, this first hydrolysis step b) can consist of a "high-temperature" hydrolysis stage, the temperature used during this stage possibly being between 100 and 115° C., in particular using a vapor-injection cooker commonly called a jet cooker. Advantageously, this stage is carried out so as to gelatinize the starch or to make the starch at least partially soluble. This stage can in particular last from 2 to 30 minutes, generally from 3 to 15 minutes. It can be carried out at a pressure of at least 1.2 bar, for example at a pressure ranging from 1.3 bar to 8 bar.

According to a second variant, this first hydrolysis step b) can comprise a first "high-temperature" hydrolysis stage and a second "low-temperature" hydrolysis stage, the temperature used during the first stage being higher than that used during the second stage. The high-temperature hydrolysis stage can be carried out as described in the previous variant. The low-temperature hydrolysis stage can be carried out in any type of conventional thermostated, preferably stirred, reactor, advantageously at a temperature of between 80 and 100° C. This second stage can in particular last from 5 to 300 minutes.

The process according to the invention comprises a step c) of inhibiting the Enzyme V. This inhibition step can be carried out by heating the solution of intermediate hydrolysate. Preferentially, the inhibition step is carried out by heating the solution of intermediate hydrolysate, for example at a temperature greater than or equal to 140° C. or even greater than or equal to 150° C. One advantage of this heating inhibition step is that it does not require successive additions of acid and base; thus, the optional subsequent step of demineralization of the hydrolysate is easier. This inhibition step can in particular be carried out by decreasing the pH of the solution of intermediate hydrolysate, in particular to a pH of less than 3.5, in combination with heating at 90° C. or higher. Advantageously, the pH is between 2.5 and 3, it is for example approximately 2.9. Preferably, the inhibition step has a duration ranging from a few minutes to a few hours, for example ranging from 30 to 120 minutes. This step is essential to the process of the invention, in order to be able to obtain the hydrolysate with the specific carbohydrate distribution of the invention. At the end of this inhibition step c), the inhibited solution of intermediate hydrolysate obtained in step c) can have a $DE_c$ that is very slightly higher than that of step b). It is generally considered that the Enzyme V is inhibited when, by placing the inhibited solution of intermediate hydrolysate at 90° C. and at a pH of 5.2 for 3 hours, its DE is less than or equal to $DE_c+1$, preferably less than or equal to $DE_c+0.5$, most preferentially equal to $DE_c$.

According to the specific process of the invention, $DE_c$ is less than the DE of the hydrolysate ($DE_e$) recovered at the end of the subsequent step f) and is therefore directly dependent thereon.

At the end of this inhibition step c), the DE of the intermediate hydrolysate can range from 3 to 20, for example from 4 to 15, in particular from 5 to 11.

Following the inhibition step, a step d) of bringing the solution of intermediate hydrolysate obtained in step c) into contact with at least one additional alpha-amylase, different than the Enzyme V, is carried out.

The additional alpha-amylase can be chosen from the *Bacillus licheniformis* enzymes, in particular those described in application WO 2011/017093 A1. Preferably, the *Bacillus licheniformis* enzymes are chosen from the enzymes of Spezyme® Alpha (Genencor®), LpHera® (Novozymes®), Liquozyme® Supra (Novozymes®) and Termamyl® (Novozymes®) type.

During step d), the additional alpha-amylase is brought into contact in amounts which make it possible to obtain the hydrolysate targeted at the end of step e). This amount can vary a great deal and is directly linked to the conditions used during this step e), in particular the time, the temperature, and/or the pH of the aqueous suspension of starch. The additional alpha-amylase is generally introduced in the form of commercial enzyme solutions. For example, it can be introduced in the form of a commercial enzyme solution in weight amounts, expressed relative to the dry weight of starch, ranging from 0.01% to 0.5%, preferably from 0.02% to 0.13%. Another way to express the amount of additional alpha-amylase is to express it in amount of enzymatic activity of "Novo Unit" (NU) type, well known to those skilled in the art. Per gram of dry starch, this amount can be in the range of from 10 to 1000 NU, for example from 50 to 500 NU. By way of example, 1 g of a solution of Liquozyme Supra® enzyme comprises at least 136 000 NU and 1 g of a solution of LpHera® enzyme comprises at least 400 000 NU.

In order to avoid any incorrect interpretation, it is specified that, when several additional alpha-amylases are used according to the process of the invention, none of these alpha-amylases brought into contact with the hydrolysate during step d) is an Enzyme V. Thus, the hydrolysis step e) is carried out in the absence of Enzyme V. Preferably, no enzyme other than the additional alpha-amylases is brought into contact with the hydrolysate during steps d) and e). The pH conditions can be selected in such a way that the alpha-amylase has an enzymatic activity during step e).

Advantageously, the hydrolysate solution formed in step d) has a pH ranging from 4.3 to 5.9.

The hydrolysate solution formed in step d) can comprise other additive compounds which assist with the enzymatic hydrolysis. For example, it can also comprise at least one calcium salt, in particular when an additional alpha-amylase which is calcium-dependent is used. The aqueous suspension of starch can also comprise sodium bisulfite.

The hydrolysate solution formed in step d) can be prepared by simply mixing the constituents.

In order to obtain the specific profile of the hydrolysate according to the invention, the process according to the invention comprises two enzymatic hydrolysis steps b) and e), carried out with various alpha-amylases. Thus, the enzymatic hydrolysis step e) is carried out in such a way that the Dextrose Equivalent $DE_e$ is greater than the Dextrose Equivalent $DE_c$ of the intermediate hydrolysate, that is to say that step e) is carried out under time and temperature conditions which make it possible to increase the Dextrose Equivalent of the hydrolysate.

Advantageously, the Dextrose Equivalent $DE_e$ is greater than or equal to $DE_c+1$, preferably greater than or equal to $DE_c+3$, in particular greater than or equal to $DE_c+5$, for example greater than or equal to $DE_c+7$. Obviously, the carbohydrate profile of the hydrolysate varies, within the previously described limits, and this depends on the difference between the Dextroses Equivalents $DE_c$ and $DE_e$. The greater this difference, the more the carbohydrate profile differs from the profile of a hydrolysate obtained by an enzymatic hydrolysis step using exclusively the Enzyme V during the hydrolysis step.

This hydrolysis step e) can be carried out by heating the intermediate hydrolysate obtained in step c). The temperature and time conditions can vary to a large extent depending on the hydrolysate targeted. They can be selected, as a function of the pH and of the amounts of additional enzymes used, so as to obtain the desired Dextrose Equivalent $DE_e$.

Preferably, said intermediate hydrolysate is heated at a temperature ranging from 50 to 120° C. This step e) is carried out until this intermediate hydrolysate is obtained. The duration of this step e) can range from 10 to 1500 minutes.

The process according to the invention comprises a step f) of recovering the hydrolysate formed in the preceding step e).

This step can also comprise a subsequent step g) of converting the hydrolysate recovered in step f).

The conversion step g) can consist of a step of purifying the hydrolysate. This step can in particular be a filtration step, for example by passing over a filter press or over a microfiltration or ultrafiltration membrane. It can also be a step of demineralization of the hydrolysate, for example by passing over an ion-exchange resin. It can also be a step of decolorizing the hydrolysate, for example by bringing the hydrolysate into contact with active carbons.

The conversion step can also consist of a step of concentrating the hydrolysate by evaporation of the water or else of a step of diluting the hydrolysate with water.

At the end of the recovery step f) or at the end of the treatment steps previously mentioned, the hydrolysate obtained is in the form of an aqueous solution.

The invention therefore also relates to a starch hydrolysate which is in the form of an aqueous solution, of which the weight amount of hydrolysate, expressed in dry weight, advantageously ranges from 20% to 85% and preferably ranges from 50% to 80%.

The process of the invention can also comprise various conversion steps among those previously described.

The process according to the invention can also comprise a conversion step g) which is a step of forming the hydrolysate in powder form, in particular by means of a spray-drying step. In the case where various conversion steps are carried out, this spray-drying step may be the final conversion step.

The hydrolysate according to the invention can thus be in the form of a powder, which can have a weight amount of hydrolysate, expressed as dry weight, of greater than 90%.

The invention will now be described in detail in the examples below. Those skilled in the art will, on reading the description of the application, easily know how to adjust the conditions of the process in order to obtain the hydrolysates of the invention.

EXAMPLES

Hydrolysate Production and Characterization
Enzymes Used
Enzyme V: Veretase® enzyme (Verenium®).
Other alpha-amylases:
LpHera® (Novozymes®);
Liquozyme® Supra (Novozymes®);
Termamyl® 120L (Novozymes®).
Methods
High Performance Liquid Chromatography
The high performance liquid chromatography system is composed of a pump of Waters M515 type, an automatic injector of Waters WISP type, a column thermostating oven set at 55° C., a differential refractometer of Waters R2414 type and a computer system equipped with software for processing the chromatograms, of Empower type (Waters). Two columns of ion-exchange resin in silver form, of Aminex HPX—42A Carbohydrate Column (300 mm×7.8 mm) type, mounted in series are used. The eluent used is distilled water (flow rate: 0.4 ml/minute). A sample of the solution of hydrolysate to be analyzed is prepared by diluting said solution with distilled water to approximately 5% solids, then by filtering it by passing it through a syringe equipped with a nozzle composed of a filtering membrane (porosity 0.45 μm). 20 μl of this solution are then injected into the apparatus for analysis.

Size Exclusion Chromatography
The size exclusion chromatography system is a high performance liquid chromatograph composed of a high-pressure pump of Waters 510 type, a Waters 717+ injector, a column thermostating oven set at 35° C., a differential refractometer of Waters R2414 type and a computer system equipped with software for processing the chromatograms, of Empower type (Waters), equipped with the SEC option. Three columns are connected in series and placed in the following order: OHpak SB-802 HQ, OHpak SB-803 HQ, OHpak SB-805 HQ (Waters). The eluent used (0.5 ml/minute) is an aqueous solution prepared from distilled water, sodium nitrate (concentration in the aqueous solution of 0.1

M) and sodium azide (concentration at 0.02% by weight). The size exclusion chromatograph is calibrated using pullulan standards. A sample of the solution of hydrolysate to be analyzed is prepared by diluting said solution with eluent to approximately 5% solids, then by filtering it by passing it through a syringe equipped with a nozzle composed of a filtering membrane (porosity 0.45 µm). 100 µl of this solution are then injected into the apparatus for analysis.

Dextrose Equivalent

The DE is measured using the NF EN ISO 5377:1981 method.

Process for Producing the Hydrolysates

Various comparative starch hydrolysates were prepared according to the following protocol 1:

An aqueous solution of starch at 18-19 degrees Baumé (that is to say approximately 33% solids) is prepared in a tank, with stirring, from dry native corn starch and demineralized water. Still with stirring, the pH is corrected (by means of a solution of HCl or of NaOH at 0.1 N) in order to adjust the pH to 5.3, or to 4.8 in the case where the alpha-amylase subsequently used is the LpHera enzyme.

Still with stirring, the commercial solution of alpha-amylase (CP1 to CP4) or the mixture of commercial solutions of alpha-amylase (CP5 to CP6) is brought into contact with the aqueous solution of starch in the weight proportions relative to the dry weight of starch that are indicated in table 1. In the case where the Termamyl 120L enzyme, which is calcium-dependent, is used, $CaCl_2$ is added beforehand to the suspension (approximately 60 ppm of calcium in the starch solution).

The hydrolysis step is carried out in the following way: the starch solution is introduced into a jet cooker. Vapor is injected into the starch solution via a nozzle in order to reach 106° C. with a counterpressure at 1.4 bar. The starch solution after bursting is kept at temperature in a contact zone for 5 to 6 minutes. The starch is dissolved during this step and is recovered on leaving the jet cooker and directly introduced into a water bath for the continuation of the hydrolysis. The temperature is regulated at 95° C. The DE of the hydrolysate increases as the hydrolysis continues. Various starch hydrolysates are recovered over time. After recovery, the enzyme is immediately inhibited by lowering the pH to 2.9 using a solution of HCl (0.1 N) and by maintaining the hydrolysate at 95° C. for 1 h.

Various starch hydrolysates according to the invention were prepared according to the following protocol 2:

An aqueous solution of starch at 18-19 degrees Baumé (that is to say approximately 33% solids) is prepared in a tank, with stirring, from dry native corn starch and demineralized water. Still with stirring, the pH is corrected (by means of a solution of HCl or of NaOH at 0.1 N) in order to adjust the pH to 5.3.

Still with stirring, the commercial solution of Enzyme V is brought into contact with the aqueous solution of starch, in weight amounts of 0.08% by weight relative to the dry weight of starch.

The hydrolysis step is carried out in the following way: the starch solution is introduced into a jet cooker. Vapor is injected into the starch solution via a nozzle in order to reach 106° C. with a counterpressure at 1.4 bar. The starch solution after bursting is kept at temperature in a contact zone for 5 to 6 minutes. The starch is dissolved during this step and is recovered on leaving the jet cooker and directly introduced into a water bath. The Enzyme V is immediately inhibited by lowering the pH to 2.9 using a solution of HCl (0.1 N) and by maintaining the hydrolysate at 95° C. for 1 h. Two intermediate hydrolysates were prepared according to this protocol; the first intermediate hydrolysate has a DE equal to 7 (for a contact time of approximately 6 minutes) and the second intermediate hydrolysate has a DE equal to 5 (for a contact time of approximately 5 minutes).

Still with stirring, the pH is corrected (by means of a solution of NaOH at 0.1 N) in order to adjust the pH to 5.3 in the case where the additional alpha-amylase subsequently used is the Liquozyme Supra enzyme or to 4.8 in the case where the alpha-amylase subsequently used is the LpHera enzyme.

According to a first example according to the invention (INV1), the commercial solution of Liquozyme Supra is brought into contact with the solution of the first intermediate hydrolysate (DE=7), in weight amounts of 0.1% by weight relative to the dry weight of starch. The hydrolysate is maintained at 95° C. and the DE of the hydrolysate increases as the hydrolysis continues. Various starch hydrolysates are recovered over time. After recovery of a hydrolysate, the enzyme is immediately inhibited by lowering the pH to 2.9 using a solution of HCl (0.1 N) and by maintaining the hydrolysate at 95° C. for 1 h.

According to a second example according to the invention (INV2), the commercial solution of LpHera is brought into contact with the solution of the second intermediate hydrolysate (DE=5), in weight amounts of 0.03% by weight relative to the dry weight of starch. The hydrolysate is maintained at 95° C. and the DE of the hydrolysate increases as the hydrolysis continues. Various starch hydrolysates are recovered over time. After recovery of a hydrolysate, the enzyme is immediately inhibited by lowering the pH to 2.9 using a solution of HCl (0.1 N) and by maintaining the hydrolysate at 95° C. for 1 h.

Hydrolysate Characteristics

The contents by dry weight of the saccharides and the DEs of the comparative hydrolysates and hydrolysates according to the invention are analyzed according to the methods described above and are reported in tables 1 and 2 below.

If these contents of DP10-20 or DP50+ are in accordance with the criteria of the invention, the number indicated in the corresponding case is indicated in bold.

TABLE 1

DE and carbohydrate profiles of the hydrolysates obtained using protocol 1 (comparative hydrolysates)

| | CP1 | | | | | CP 2 | | | | CP3 | | | | | CP4 | | | | |
|---|---|---|---|---|---|---|---|---|---|---|---|---|---|---|---|---|---|---|---|
| | | | | | | | | Enzyme | | | | | | | | | | | |
| | Termamyl 120 L (0.1%) | | | | | Liquozyme Supra (0.1%) | | | | Veretase (0.08%) | | | | | LpHera (0.03%) | | | | |
| DE | 12 | 17 | 19 | 21 | 28 | 16 | 19.2 | 22.7 | 25.8 | 13.9 | 18.7 | 20.1 | 22 | 29.3 | 12.1 | 17.5 | 20.6 | 23.7 | 28.1 |
| DP1-2 | 3.8 | 5.7 | 6.5 | 7.6 | 11.2 | 4.2 | 6.1 | 9.2 | 9.9 | 3.9 | 5.5 | 6.7 | 7.7 | 12.6 | 2.3 | 4.6 | 6.7 | 9.1 | 12.9 |
| DP3-6 | 16.5 | 26.2 | 27.4 | 32.1 | 53.3 | 21.2 | 30.2 | 38.1 | 39.8 | 13.0 | 17.5 | 20.7 | 23.5 | 34.3 | 16.3 | 26.8 | 32.5 | 37.7 | 45.0 |
| DP7-9 | 11.9 | 14.2 | 13.8 | 13.7 | 5.7 | 17.2 | 18.3 | 14.9 | 13.6 | 19.4 | 24.6 | 26.9 | 28.3 | 29.1 | 16.7 | 19.6 | 18.2 | 15.4 | 9.5 |
| DP11+ | ND | ND | ND | ND | ND | 53.4 | 42.7 | 35.9 | 34.9 | 54.7 | 42.1 | 36.1 | 30.8 | 15.7 | 61.6 | 47.3 | 41 | 36.5 | 30.5 |

TABLE 1-continued

DE and carbohydrate profiles of the hydrolysates obtained using protocol 1 (comparative hydrolysates)

| | CP1 | | | | | CP 2 | | | | CP3 | | | | | CP4 | | | | |
|---|---|---|---|---|---|---|---|---|---|---|---|---|---|---|---|---|---|---|---|
| | Termamyl 120 L (0.1%) | | | | | Liquozyme Supra (0.1%) | | | | Veretase (0.08%) | | | | | LpHera (0.03%) | | | | |
| DE | 12 | 17 | 19 | 21 | 28 | 16 | 19.2 | 22.7 | 25.8 | 13.9 | 18.7 | 20.1 | 22 | 29.3 | 12.1 | 17.5 | 20.6 | 23.7 | 28.1 |
| DP10-20 | 22.4 | 19.6 | 18.4 | 16.7 | 10.8 | 14 | 9.1 | 8.8 | 9.1 | 41.6 | 40.8 | 37.5 | 34.6 | 22.5 | 10.7 | 6.5 | 6.5 | 7.5 | 9.5 |
| −0.83 × DE + 27.5 | 17.5 | 13.3 | 11.7 | 10.1 | 4.3 | 14.2 | 11.6 | 8.7 | 6.1 | 16.0 | 12.0 | 10.8 | 9.2 | 3.2 | 17.5 | 13.0 | 10.4 | 7.8 | 4.2 |
| −1.25 × DE + 55 | 40.0 | 33.8 | 31.3 | 28.8 | 20.0 | 35.0 | 31.0 | 26.6 | 22.8 | 37.6 | 31.6 | 29.9 | 27.5 | 18.4 | 39.9 | 33.1 | 29.3 | 25.4 | 19.9 |
| DP21-30 | 6.9 | 5.8 | 5.5 | 4.8 | 3.3 | 4.5 | 3.7 | 3.8 | 3.9 | 10.1 | 6.9 | 5.4 | 4.1 | 1.2 | 3.4 | 2.7 | 3.1 | 3.6 | 4 |
| DP31-40 | 3.7 | 3.5 | 3.5 | 3.7 | 2.5 | 3.1 | 3 | 3.3 | 3.2 | 4.8 | 2.5 | 1.8 | 1.2 | 0.2 | 2.1 | 2.6 | 2.8 | 3 | 3 |
| DP41-50 | 2.9 | 2.8 | 2.6 | 2.5 | 2.0 | 2.7 | 3 | 2.8 | 2.7 | 2.3 | 0.9 | 0.6 | 0.3 | 0 | 1.6 | 2.5 | 2.7 | 2.7 | 2.4 |
| DP50+ | 31.8 | 22.2 | 22.4 | 18.8 | 11.1 | 33.3 | 26.6 | 19.2 | 18 | 5.1 | 1.3 | 0.7 | 0.4 | 0 | 46.7 | 34.8 | 27.4 | 21.1 | 13.6 |
| −0.83 × DE + 25 | 15.0 | 10.9 | 9.2 | 7.6 | 1.8 | 11.7 | 9.1 | 6.2 | 3.6 | 13.5 | 9.5 | 8.3 | 6.7 | 0.7 | 15.0 | 10.5 | 7.9 | 5.3 | 1.7 |
| −1.07 × DE + 40 | 27.2 | 21.8 | 19.7 | 17.5 | 10.0 | 22.9 | 19.5 | 15.7 | 12.4 | 25.1 | 20.0 | 18.5 | 16.5 | 8.6 | 27.1 | 21.3 | 18.0 | 14.6 | 9.9 |

TABLE 2

DE and carbohydrate profiles of the hydrolysates obtained using protocol 1 with mixtures of enzymes (comparative hydrolysates) and protocol 2 (hydrolysates according to the invention)

| | CP5 | | | | INV1 | | | | CP6 | | | | INV2 | | | |
|---|---|---|---|---|---|---|---|---|---|---|---|---|---|---|---|---|
| | 0.08% Liquozyme Supra + 0.02% Veretase | | | | Veretase/inhibition/ Liquozyme Supra | | | | 0.05% Liquozyme Supra + 0.05% Veretase | | | | Veretase/ inhibition/LpHera | | | |
| DE | 12.4 | 20.2 | 22.8 | 26.1 | 16.9 | 19.8 | 22.4 | 27.4 | 15 | 18.2 | 22.3 | 28.7 | 12.7 | 20.6 | 21.9 | 24.7 | 28.1 |
| DP1-2 | 3.0 | 6.2 | 7.6 | 10.4 | 3.6 | 5.9 | 7.1 | 11.5 | 3.5 | 5.0 | 7.1 | 12.5 | 2.5 | 5.4 | 6.9 | 10.1 | 11.0 |
| DP3-6 | 11.9 | 28.8 | 31.6 | 39.2 | 22.8 | 31.7 | 36.7 | 49.8 | 13.4 | 18.3 | 25.1 | 39.9 | 16.3 | 29.4 | 35.7 | 42.2 | 46.4 |
| DP7-9 | 16.7 | 24.6 | 25.6 | 24.6 | 21.9 | 23.1 | 21.9 | 12.7 | 18.8 | 23.3 | 27.7 | 26.4 | 18.8 | 24.3 | 23.1 | 18.3 | 14.9 |
| DP11+ | 61.3 | 33.9 | 27.6 | 19.0 | 45.7 | 34.9 | 30.4 | 22.4 | 55.8 | 44.8 | 31.0 | 13.6 | 56.3 | 36.6 | 30.7 | 25.5 | 23.9 |
| DP10-20 | 35.4 | 24.1 | 24.9 | 20.8 | 21.5 | 16.2 | 13.9 | 12.5 | 39.5 | 38.0 | 32.4 | 19.8 | 23.8 | 15.2 | 12.7 | 12.9 | 13.1 |
| −0.83 × DE + 27.5 | 17.2 | 10.7 | 8.6 | 5.8 | 13.5 | 11.1 | 8.9 | 4.8 | 15.1 | 12.4 | 9.0 | 3.7 | 17.0 | 10.4 | 9.3 | 7.0 | 4.2 |
| −1.25 × DE + 55 | 39.5 | 29.8 | 26.5 | 22.4 | 33.9 | 30.3 | 27.0 | 20.8 | 36.3 | 32.3 | 27.1 | 19.1 | 39.1 | 29.3 | 27.6 | 24.1 | 19.9 |
| DP21-30 | 10.7 | 6.0 | 4.9 | 2.9 | 6.8 | 5.1 | 4.6 | 3.8 | 10.4 | 7.9 | 4.8 | 1.1 | 8.9 | 5.5 | 4.8 | 4.4 | 4.2 |
| DP31-40 | 6.0 | 3.1 | 2.1 | 1.0 | 4.3 | 3.5 | 3.2 | 2.4 | 5.0 | 3.3 | 1.6 | 0.2 | 5.3 | 3.7 | 3.2 | 2.7 | 2.5 |
| DP41-50 | 3.3 | 1.8 | 1.1 | 0.4 | 2.9 | 2.4 | 2.2 | 1.6 | 2.5 | 1.4 | 0.6 | 0.1 | 3.2 | 2.5 | 2.1 | 1.8 | 1.5 |
| DP50+ | 13.0 | 5.5 | 2.4 | 0.8 | 16.3 | 12.1 | 10.5 | 6.0 | 6.8 | 2.9 | 0.9 | 0.0 | 21.2 | 14.1 | 11.5 | 7.6 | 6.6 |
| −0.83 × DE + 25 | 14.7 | 8.2 | 6.1 | 3.3 | 11.0 | 8.6 | 6.4 | 2.3 | 12.6 | 9.9 | 6.5 | 1.2 | 14.5 | 7.9 | 6.8 | 4.5 | 1.7 |
| −1.07 × DE + 40 | 26.7 | 18.4 | 15.6 | 12.1 | 21.9 | 18.8 | 16.0 | 10.7 | 24.0 | 20.5 | 16.1 | 9.3 | 26.4 | 18.0 | 16.6 | 13.6 | 9.9 |

These tables demonstrate that only the hydrolysates of the invention have the specific carbohydrate profile and combine all of the criteria DP10-20 or DP50+. In particular, the hydrolysate produced using the Termamyl 120 L enzyme systematically exhibits amounts of saccharides of DP50+ type which are always greater than that of the criterion according to the invention.

Figure 2:
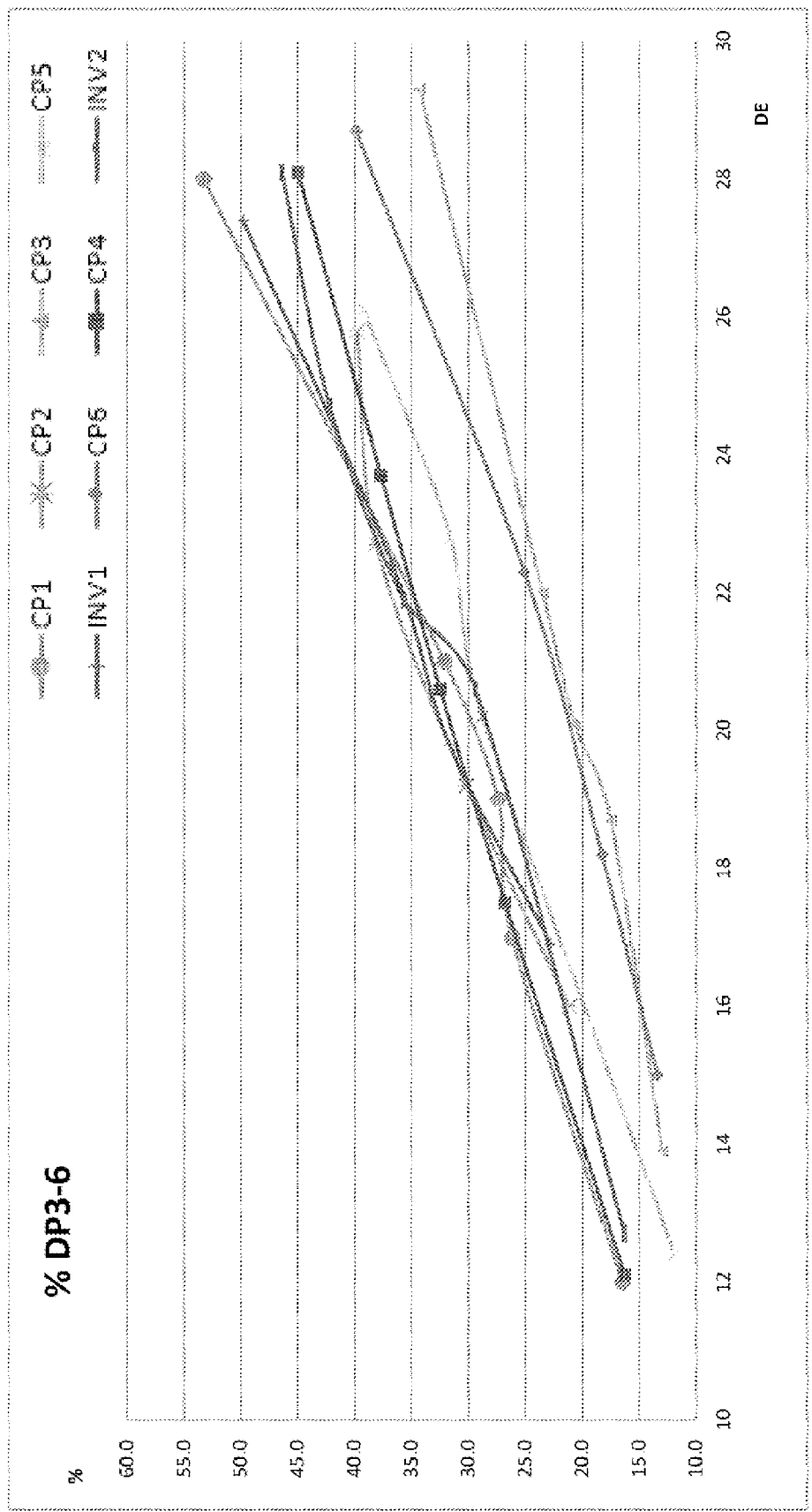
FIG. 2 represents the change in the dry weight content of DP3-6 as a function of the DE of hydrolysates according to the invention and comparative hydrolysates.
Figure 3:
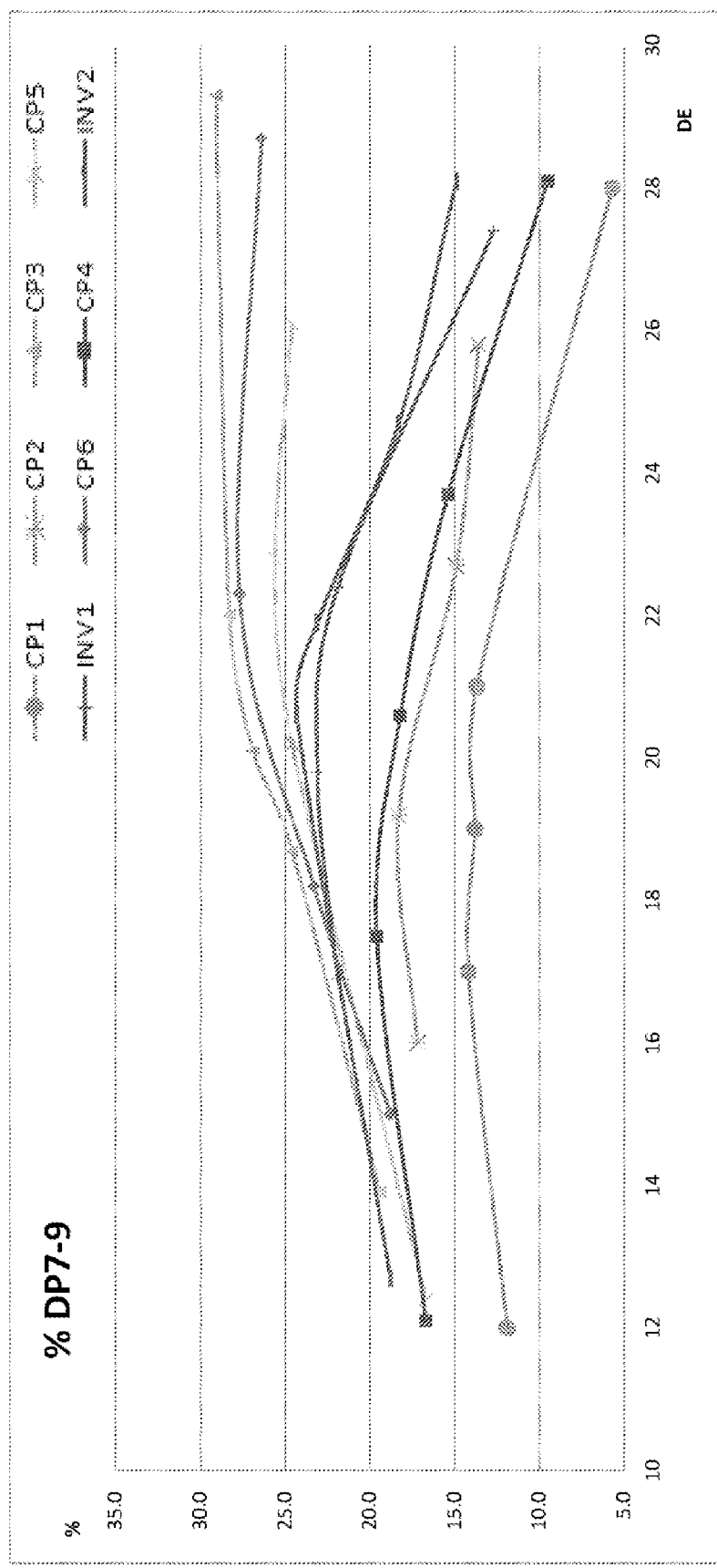
FIG. 3 represents the change in the dry weight content of DP7-9 as a function of the DE of hydrolysates according to the invention and comparative hydrolysates.
Figure 4:
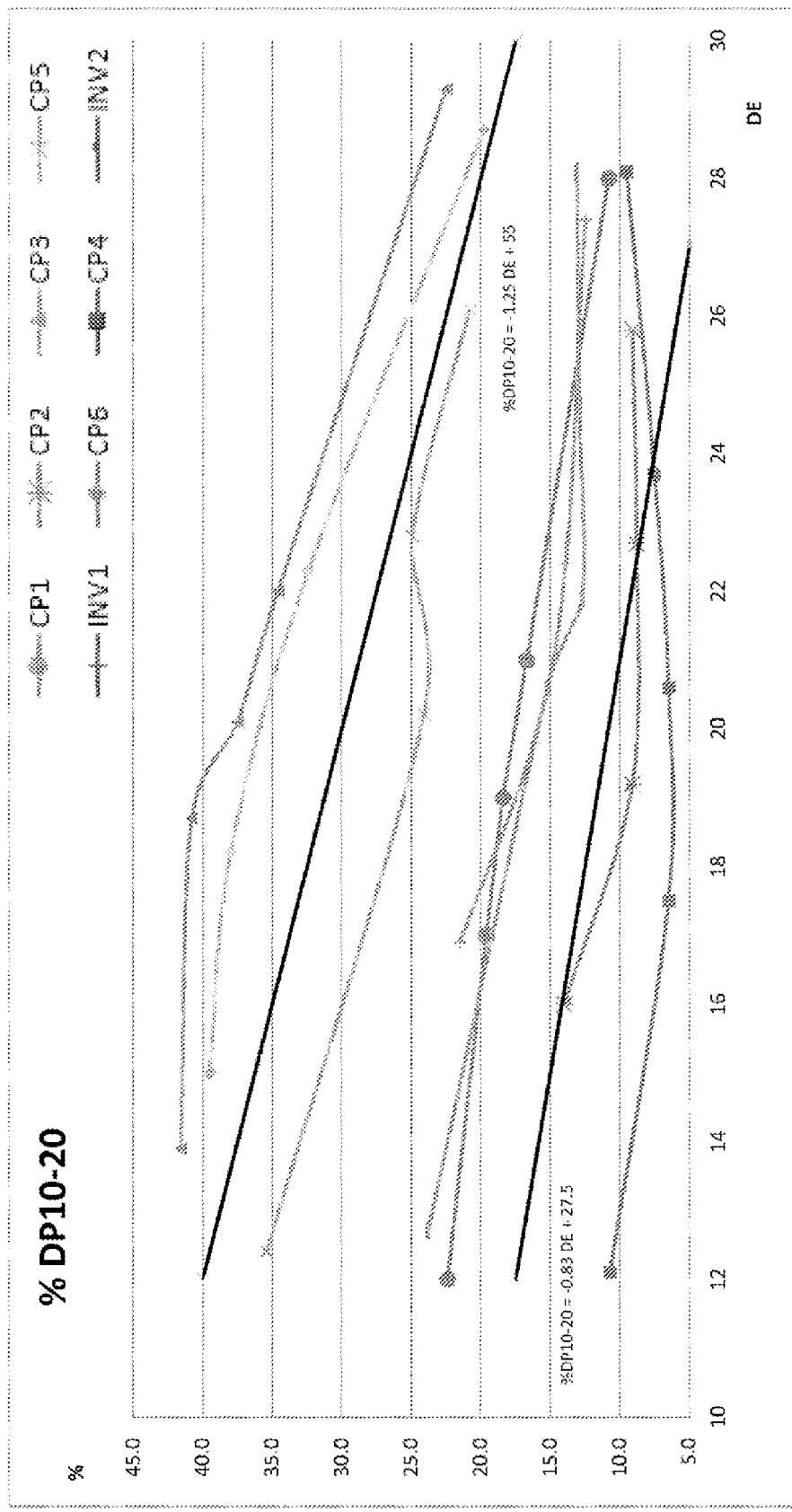
FIG. 4 represents the change in the dry weight content of DP10-20 as a function of the DE of hydrolysates according to the invention and comparative hydrolysates.
Figure 5:
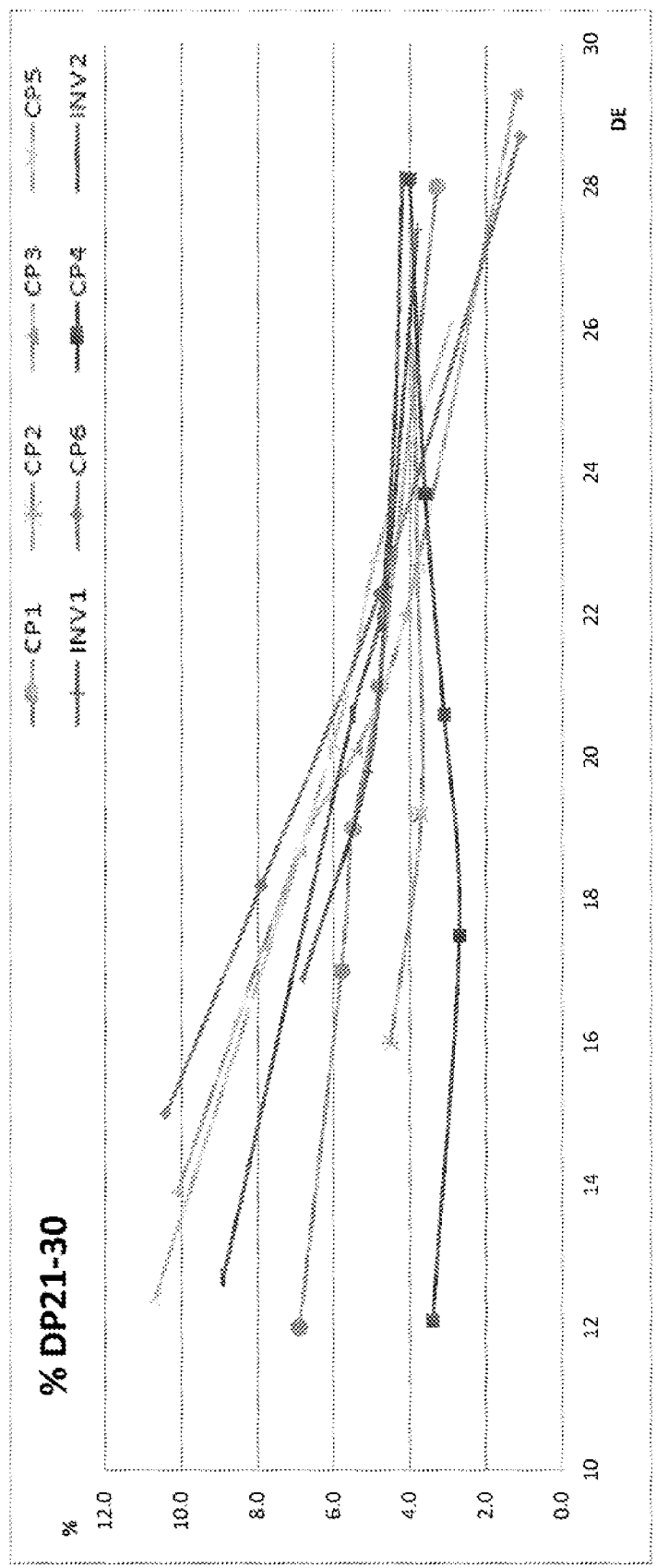
FIG. 5 represents the change in the dry weight content of DP21-30 as a function of the DE of hydrolysates according to the invention and comparative hydrolysates.
Figure 6:
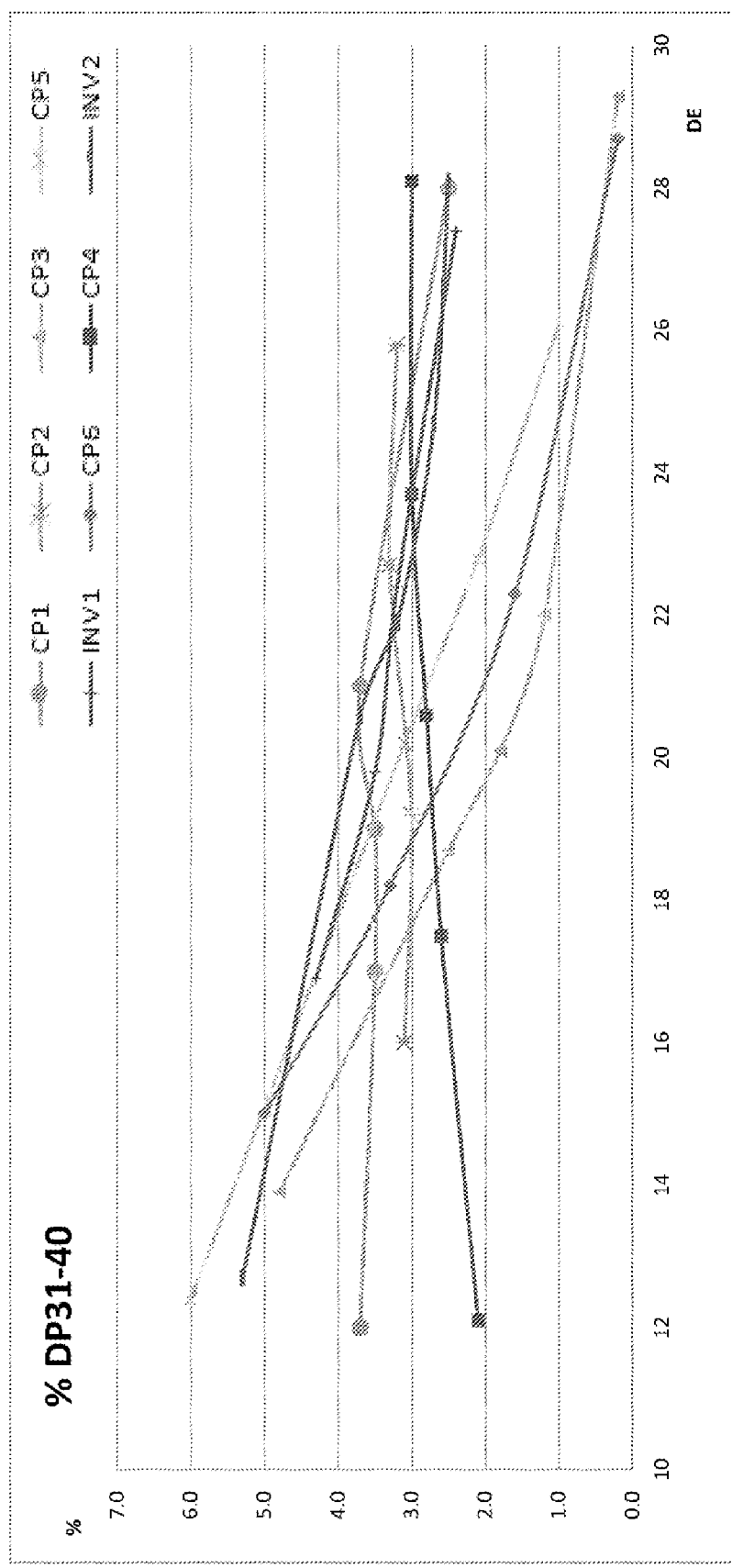
FIG. 6 represents the change in the dry weight content of DP31-40 as a function of the DE of hydrolysates according to the invention and comparative hydrolysates.
Figure 7:
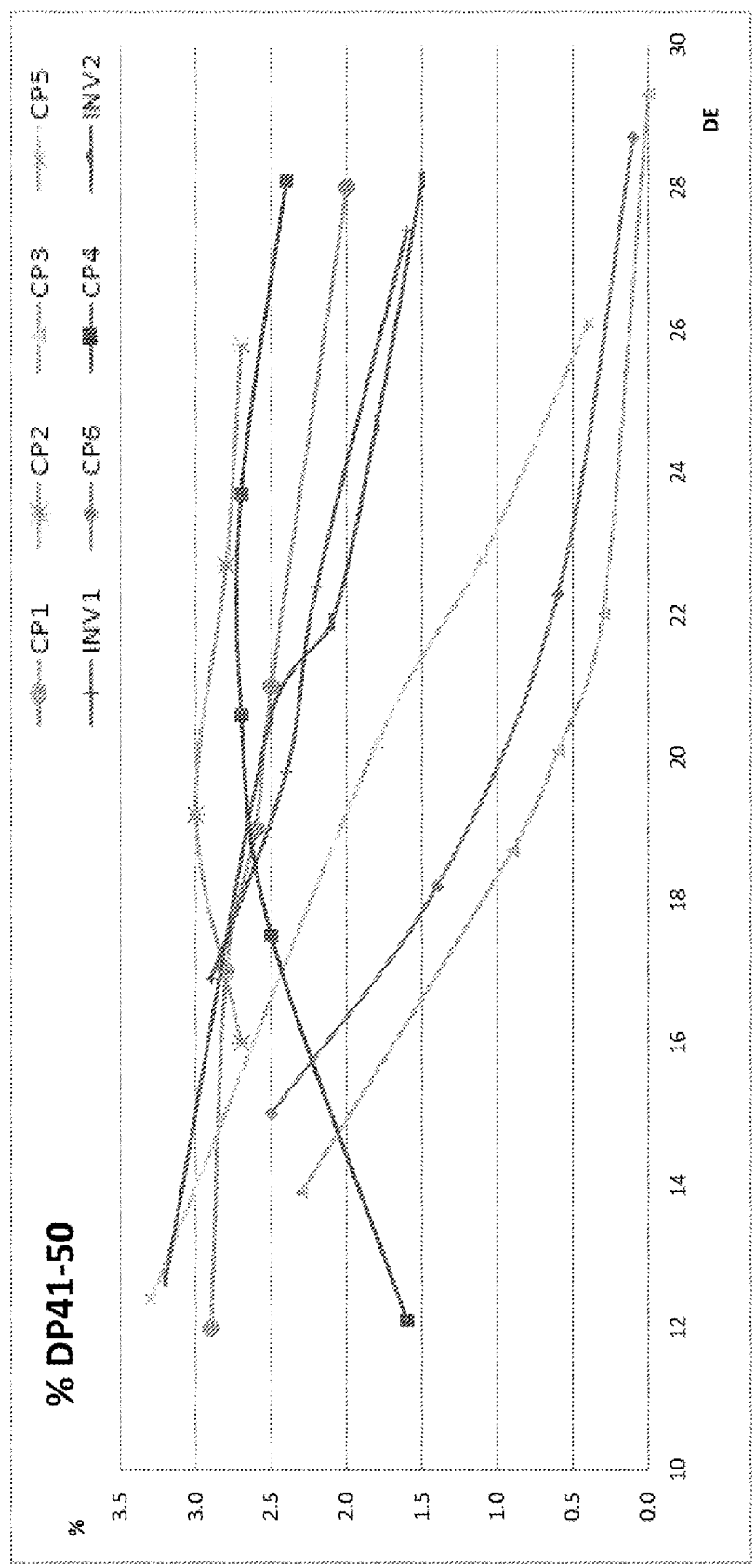
FIG. 7 represents the change in the dry weight content of DP41-50 as a function of the DE of hydrolysates according to the invention and comparative hydrolysates.
Figure 8:
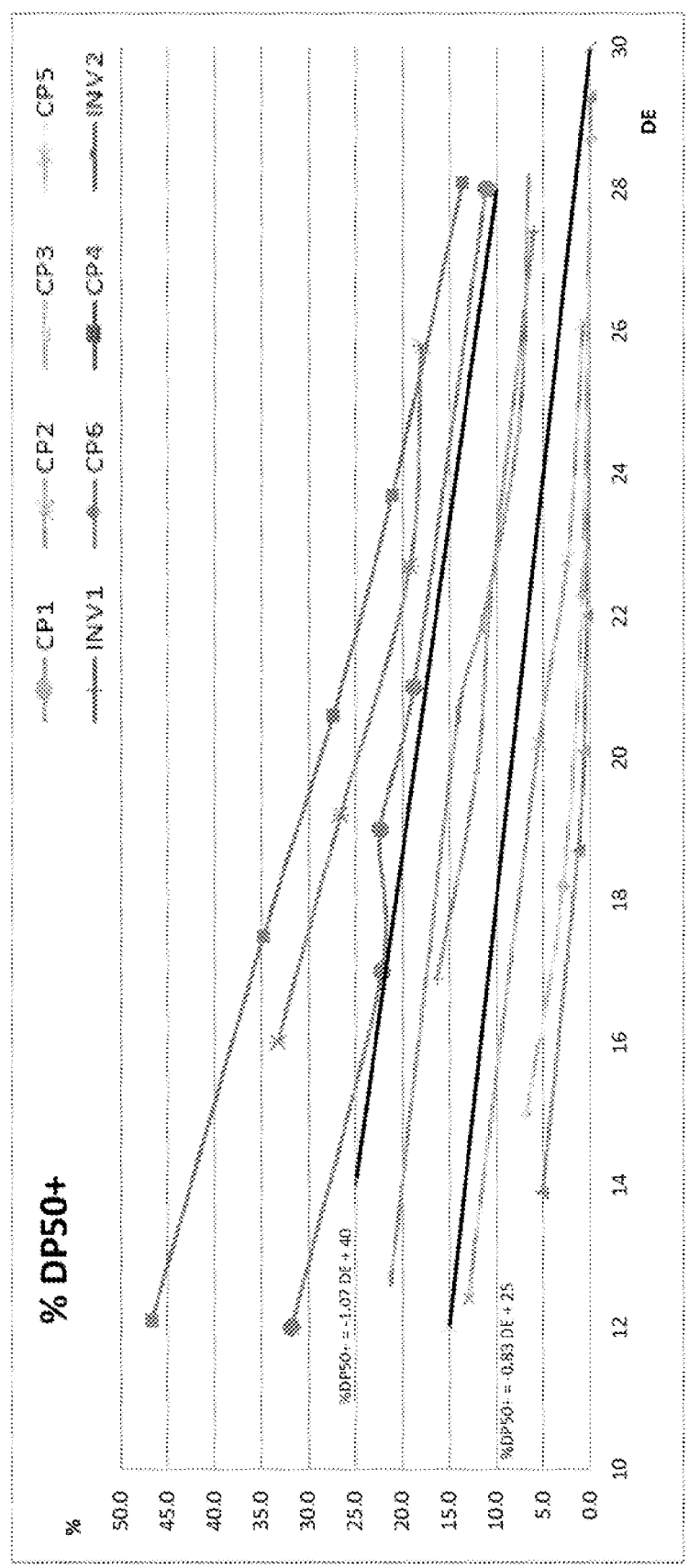
FIG. 8 represents the change in the dry weight content of DP50+ as a function of the DE of hydrolysates according to the invention and comparative hydrolysates.

FIGS. 1 to 8 show the changes in the dry weight contents of DPX-Y as a function of the DE of the hydrolysates according to the invention and comparative hydrolysates. The figures, in particular FIGS. 4 and 8, clearly attest to the specific carbohydrate profile of the hydrolysate according to the invention.

Starch Hydrolysate Retrogradation Test

Hydrolysates of the INV1, CP3 and CP5 tests are recovered and filtered under vacuum by passing them through a diatomaceous earth cake. These hydrolysates respectively have a DE of 22.4, 22.0 and 22.8. They are in the form of concentrated solutions at 30% solids content, which are therefore clear. These solutions are placed at 4° C. for 6 hours in order to accelerate the possible retrogradation. After this treatment, it is observed whether or not the solution is retrograded, that is to say whether or not it has remained clear. The observations are reported in table 3.

TABLE 3

Retrogradation behavior

| | Hydrolysate No. | | |
|---|---|---|---|
| | INV 1 | CP3 | CP5 |
| Appearance of the solution | Clear | Cloudy | Cloudy |

These tests demonstrate that the hydrolysate according to the invention has improved retrogradation behavior. Indeed, the hydrolysate CP3 obtained using the Enzyme V and the hydrolysate CP5 obtained using a mixture of Enzyme V and *Bacillus licheniformis* described in application WO 2011/017093 becomes cloudy during the test; conversely, the solution of hydrolysate according to the invention still remains clear after 6 hours.

Sensory Test (Taste and Odor)

It is desired to measure the impact of the change in carbohydrate profile on the taste and the odor of two glucose syrups (DE approximately equal to 28).

Products

The two products tested are the hydrolysates INV1 having a DE equal to 27.4 and CP1 having a DE equal to 28.

Materials & Methods

Implementation

The two products were dissolved so as to achieve a final brix of 27.5. The water used for the dissolution of the products is demineralized before adding to the product.

The sensory analysis was carried out by triangle test according to standard ISO 4120: 2004.

For the odor triangle test, the solutions are presented to the panellists in closed glass bottles kept in a water bath at 60° C.

For the taste triangle test, the solutions are presented to the panellists in closed glass bottles kept at ambient temperature.

Panel

The panel consists of participants who regularly sit on quality control panels regarding starch hydrolysates.

Tasting Conditions

Individual tasting cubicles, white walls, calm environment (to facilitate concentration)

Colored bottles (so as not to be influenced by seeing the product)

Products rendered anonymous with a 3-figure code (to prevent the code from influencing the assessment of the products)

Products presented in a random order (to prevent order and persistence effects)

Exercise

The method used to compare the two products is the triangle test. Three samples are simultaneously presented to the tasters; 2 of the 3 samples are identical. The exercise consists in identifying which sample is different from the other two. In order to avoid any bias, the test was carried out in equilibrated blocks (the different sample is either sample A or sample B; it is in first, in second or in third position randomly—AAB, ABA, ABB, BAA, BAB, BBA).

Data Processing

When replying randomly to the question "which is the different sample?", there is a 1 in 3 chance of finding the correct answer. Consequently, the probability of having BR correct answers according to N panellists by chance follows a binomial law BR~B(N,1/3). The usual confidence threshold is 0.05.

Results

Odor

A difference is clearly perceptible between the products tested; the hydrolysate according to the invention INV1 induces less off flavors (cleaning product, cement), it has a more neutral, less pronounced odor.

Taste

A difference is clearly perceptible between the products tested. According to the panel participants, the product according to the invention INV1 is slightly sweeter and the comparative product also has a slight taste of paper (also linked to the texture of the hydrolysate), of caramel or even of laundry detergent.

This test demonstrates that, in comparison with a hydrolysate having the same DE and produced with a conventional enzyme of Termamyl 120 L type, the hydrolysate according to the invention has a sweeter taste. This is all the more surprising since the amounts of sugars (DP1-2) in the hydrolysates according to the invention are, for their part, entirely similar to those of the comparative hydrolysates CP1.

The invention claimed is:

1. A starch hydrolysate having a Dextrose Equivalent DE ranging from 5 to 30 and in which the DE, the dry weight content of saccharides having a degree of polymerization ranging from 10 to 20 (DP 10-20) and the dry weight content of saccharides having a degree of polymerization of 50 or more (DP 50+) are such that they meet the following inequations:

$$-0.83 \times DE + 25 \leq \% \; DP50+ \leq -1.07 \times DE + 40;$$

$$-0.83 \times DE + 27.5 \leq \% \; DP10\text{-}20 \leq -1.25 \times DE + 55.$$

2. The starch hydrolysate as claimed in claim 1, having:
a DE ranging from 24 to 30;
a dry weight content of DP 10-20 ranging from 10% to 18%;
a dry weight content of DP 50+ ranging from 3% to 13%.

3. The starch hydrolysate as claimed in claim 1, having:
a DE ranging from 20 to 24;
a dry weight content of DP 10-20 ranging from 10% to 20%;
a dry weight content of DP 50+ranging from 6% to 18%.

4. The starch hydrolysate as claimed in claim 1, having:
a DE ranging from 17 to 20;
a dry weight content of DP 10-20 ranging from 12% to 25%;
a dry weight content of DP 50+ ranging from 10% to 19%.

5. The starch hydrolysate as claimed in claim 1, having:
a DE ranging from 15 to 17;
a dry weight content of DP 10-20 ranging from 16% to 27%;
a dry weight content of DP 50+ ranging from 13% to 22%.

6. The starch hydrolysate as claimed in claim 1, having:
a DE ranging from 13 to 15;
a dry weight content of DP 10-20 ranging from 17% to 30%;
a dry weight content of DP 50+ ranging from 17% to 25%.

7. The starch hydrolysate as claimed in claim 1, having:
a DE ranging from 10 to 13;
a dry weight content of DP 10-20 ranging from 20% to 32%;
a dry weight content of DP 50+ ranging from 18% to 28%.

8. The hydrolysate as claimed in claim 1, characterized in that it is in the form of an aqueous solution.

9. The hydrolysate as claimed in claim 1, characterized in that it is in the form of a powder.

10. A process for producing the starch hydrolysate according to claim 1, comprising:
a) a step of bringing an aqueous solution of starch or of starchy material into contact with at least one alpha-amylase comprising an Enzyme V;
b) followed by a step of hydrolysis of said aqueous solution;
c) followed by a step of inhibition of the Enzyme V so as to form a solution of intermediate hydrolysate having a DE equal to $DE_c$;
d) followed by a step of bringing the solution of intermediate hydrolysate obtained in step c) into contact with at least one additional alpha-amylase, different than the Enzyme V;
e) followed by a second hydrolysis step so as to form a hydrolysate for a period of time sufficient for it to have a $DE_e$ ranging from 5 to 30;
f) followed by a step of recovering the hydrolysate formed in step e); characterized in that the Enzyme V is an enzyme chosen from:
polypeptides encoded by a nucleotide sequence as represented in SEQ ID NO1 or a nucleotide sequence having a percentage identity relative to the sequence SEQ ID NO1 at least equal to 80%, or
polypeptides comprising the enzymatically active fragment of the nucleotide sequence encoded by the sequence SEQ ID NO1.

11. The process as claimed in claim 10, characterized in that the aqueous solution of starch formed in step a) has a pH ranging from 4.3 to 5.9.

12. The process as claimed in claim 10, characterized in that the solution of hydrolysate formed in step d) has a pH ranging from 4.3 to 5.9.

13. The process as claimed in claim 10, characterized in that the inhibition step is carried out by heating the solution of intermediate hydrolysate at a temperature greater than or equal to 150° C.

14. The process as claimed in claim 10, characterized in that the $DE_e$ is greater than or equal to $DE_c+3$.

15. The process as claimed in claim 10, characterized in that it also comprises at least one step g) of converting the hydrolysate recovered in step f).

16. The process as claimed in claim 15, characterized in that step g) is a step of forming the hydrolysate in powder form by means of a spray-drying step.

17. A food product, comprising the starch hydrolysate as claimed in claim 1 and at least one food ingredient.

18. A pharmaceutical product, comprising the starch hydrolysate as claimed in claim 1 and at least one pharmaceutical ingredient.

19. A mixture, comprising the starch hydrolysate as claimed in claim 1 and a second hydrolysate.

20. The process according to claim 10, wherein the percentage identity is at least 85%.

21. The process according to claim 10, wherein the percentage identity is at least 90%.

22. The process according to claim 10, wherein the percentage identity is at least 98%.

23. The process according to claim 10, wherein the percentage identity is at least 99%.

* * * * *

SEQUENCE LISTING

```
<160> NUMBER OF SEQ ID NOS: 1

<210> SEQ ID NO 1
<211> LENGTH: 1311
<212> TYPE: DNA
<213> ORGANISM: Artificial Sequence
<220> FEATURE:
<223> OTHER INFORMATION: synthetic

<400> SEQUENCE: 1
atggccaagt actccgagct ggaaaagggc ggggtcataa tgcaggcgtt ctactgggac      60
gtgccttcag gaggaatatg gtgggacaca atacggcaga agataccgga gtggtacgat     120
gccggaatct ccgcaatatg gattccccg gcgagcaagg gcatgggcgg cgcctattcg      180
atgggctacg accctacga cttctttgac ctcggtgagt acgaccagaa gggaacggta      240
gagacgcgct ttggctccaa gcaggagctc gtgaacatga taaacaccgc ccacgcctat     300
ggcatgaagg taatagccga tatagtcatc aaccaccgcg ccggcggtga cctggagtgg     360
aaccccttcg tgaacgacta tacctggacc gacttctcaa aggtcgcgtc gggtaaatac     420
acggccaact acctcgactt ccacccgaac gagctccatg cgggcgattc cggaacattt     480
ggaggctatc ccgacatatg ccacgacaag agctgggacc agtactggct ctgggccagc     540
caggagagct acgcggcata tctcaggagc atcggcatcg atgcctggcg cttcgactac     600
```

-continued

```
gtcaagggct atgctccctg ggtcgtcaag gactggctga actggtgggg aggctgggcg      660
gttggagagt actgggacac caacgtcgac gctgttctca actgggcata ctcgagcggt      720
gccaaggtct ttgacttcgc cctctactac aagatggatg aggcctttga caacaaaaac      780
attccagcgc tcgtctctgc ccttcagaac ggccagactg ttgtctcccg cgacccgttc      840
aaggccgtaa cctttgtagc aaaccacgac accgatataa tctggaacaa gtatccagcc      900
tacgcgttca tcctcaccta cgagggccag ccgacaatat tctaccgcga ctacgaggag      960
tggctcaaca aggataagct caagaacctc atctggatac atgagaacct cgccggagga     1020
agcaccgaca tagtctacta cgataacgat gaactcatct tcgtcaggaa cggctacggg     1080
gacaagccgg ggcttataac ctacatcaac ctaggctcga gcaaggccgg aaggtgggtt     1140
tatgtgccga agttcgcggg cgcgtgcatc cacgagtata ctggtaacct cggaggctgg     1200
gtagacaagt acgtctactc aagcggctgg gtctatctcg aagctccagc ttacgaccct     1260
gccaacgggc agtatggcta ctccgtgtgg agctactgcg gggtgggctg a              1311
```